(12) United States Patent
Le Devedec et al.

(10) Patent No.: US 12,343,315 B2
(45) Date of Patent: *Jul. 1, 2025

(54) TOPICAL CANNABINOID COMPOSITIONS FOR CLEAR SKIN

(71) Applicant: Avicanna Inc., Toronto (CA)

(72) Inventors: Frantz Henri Emmanuel Le Devedec, North York (CA); Akm Abdul Hai, Etobicoke (CA); Aras Azadian, Toronto (CA); Setu Nimish Purohit, Toronto (CA); Justin Michael Grant, Toronto (CA); Samantha Carolyn Watt, Toronto (CA)

(73) Assignee: Avicanna Inc., Toronto (CA)

( * ) Notice: Subject to any disclaimer, the term of this patent is extended or adjusted under 35 U.S.C. 154(b) by 482 days.

This patent is subject to a terminal disclaimer.

(21) Appl. No.: 17/075,764

(22) Filed: Oct. 21, 2020

(65) Prior Publication Data

US 2021/0113490 A1   Apr. 22, 2021

Related U.S. Application Data

(60) Provisional application No. 62/923,905, filed on Oct. 21, 2019.

(51) Int. Cl.
| | | |
|---|---|---|
| *A61K 31/05* | (2006.01) | |
| *A61K 8/04* | (2006.01) | |
| *A61K 8/34* | (2006.01) | |
| *A61K 8/9789* | (2017.01) | |
| *A61K 9/06* | (2006.01) | |
| *A61K 31/015* | (2006.01) | |
| *A61K 36/53* | (2006.01) | |
| *A61K 36/61* | (2006.01) | |
| *A61P 17/10* | (2006.01) | |
| *A61Q 19/00* | (2006.01) | |

(52) U.S. Cl.
CPC ............ *A61K 31/05* (2013.01); *A61K 8/042* (2013.01); *A61K 8/347* (2013.01); *A61K 8/9789* (2017.08); *A61K 9/06* (2013.01); *A61K 31/015* (2013.01); *A61K 36/53* (2013.01); *A61K 36/61* (2013.01); *A61P 17/10* (2018.01); *A61Q 19/00* (2013.01)

(58) Field of Classification Search
CPC ...... A61K 31/05; A61K 8/9789; A61K 8/042; A61K 8/347; A61K 9/06; A61K 31/015; A61K 36/53; A61K 36/61; A61K 8/9787; A61P 17/10; A61Q 19/00

See application file for complete search history.

(56) References Cited

U.S. PATENT DOCUMENTS

| | | |
|---|---|---|
| 9,730,911 B2 | 8/2017 | Verzura et al. |
| 10,555,928 B2 | 2/2020 | Blackmon et al. |
| 2016/0106705 A1 | 4/2016 | Verzura et al. |
| 2017/0360745 A1 | 12/2017 | Blackmon et al. |
| 2019/0247325 A1 | 8/2019 | Kleidon |
| 2019/0275095 A1 | 9/2019 | Spencer et al. |
| 2019/0307719 A1 | 10/2019 | Karelis et al. |
| 2019/0374552 A1 | 12/2019 | Hoag |
| 2020/0215026 A1 | 7/2020 | Blackmon et al. |
| 2020/0253921 A1 | 8/2020 | May et al. |
| 2020/0327987 A1 | 10/2020 | May et al. |
| 2021/0046040 A1 | 2/2021 | Avram |

FOREIGN PATENT DOCUMENTS

| | | | | |
|---|---|---|---|---|
| WO | 2017218853 | | 12/2017 | |
| WO | 2018023164 | | 2/2018 | |
| WO | WO-2018023164 A1 * | 2/2018 | ............ A61K 31/01 |
| WO | 2018085535 | | 5/2018 | |
| WO | WO-2018085535 A2 * | 5/2018 | ........... A61K 31/015 |
| WO | 2019089583 | | 5/2019 | |
| WO | WO-2019089583 A1 * | 5/2019 | ........... A61K 31/015 |
| WO | 2019195943 | | 10/2019 | |
| WO | 2020012480 | | 1/2020 | |

OTHER PUBLICATIONS

PCT International Application No. PCT/IB20/060668, International Search Report and Written Opinion of the International Searching Authority, dated Jul. 15, 2021, 12 pages.

* cited by examiner

*Primary Examiner* — Jeffrey S Lundgren
*Assistant Examiner* — Ibrahim D Bori
(74) *Attorney, Agent, or Firm* — DLA PIPER LLP (US)

(57) ABSTRACT

Topical composition comprising cannabinoids in combination with one or more antioxidants, one or more antimicrobial agents, one or more anti-inflammatory agents and one or more skin conditioning agents are provided. Also provided are methods comprising applying a topical composition provided herein to the skin of a subject and uses of a topical composition for promoting hydration and clear skin.

10 Claims, No Drawings

TOPICAL CANNABINOID COMPOSITIONS FOR CLEAR SKIN

CROSS-REFERENCE TO RELATED APPLICATIONS

This application claims priority to U.S. Provisional Application Ser. No. 62/923,905, filed Oct. 21, 2019, the content of which is herein incorporated by reference in its entirety.

FIELD

The present disclosure relates to topical cannabinoid compositions and methods for promoting hydration and clear skin.

BACKGROUND

The skin provides the body with mechanical protection and acts as a chemical barrier to restrict foreign substance penetration, to prevent water or fluid loss and to maintain a constant temperature.

The skin of the body and more particularly that of the face is constantly subjected to deterioration due to environment, such as from wind, cold or dust, leading to a significant water loss from the skin. This deterioration can change the visual appearance, physical properties, or physiological functions of skin in ways that are considered visually undesirable. The most notable and obvious changes include the development of various forms of skin conditions including acne vulgaris, acne conglobata, erythema, rosacea, fine lines, wrinkles, scarring, photoaging, loss of water, loss of elasticity, increased sagging, increased oiliness, loss of firmness, loss of color evenness or tone, coarse surface texture, and mottled pigmentation.

There is consequently ongoing research to introduce into cosmetic or dermatological industry new compositions which prevent deterioration of the skin due to environment. Several topical compositions are currently available. These compositions have various drawbacks ranging from unpleasant tactile properties (e.g., heavy, greasy, or sticky feel), instability issues, skin-irritation issues, insufficient moisturization capabilities, or the compositions are too harsh for sensitive skin.

Thus, a product that has no or fewer adverse effects and does not cause skin irritation would be advantageous. There is also a need to use natural remedies as alternative or complementary therapy to restore skin's appearance, physical properties, or physiological functions. With relaxation of laws regulating *cannabis* use, there now exists the opportunity to explore the potential of cannabinoids to address such skin problems.

SUMMARY

In one aspect, there is provided a topical cannabinoid composition comprising:
  a. a cannabinoid at 0.1-10% (w/w),
  b. an antioxidant at 0.01-5% (w/w),
  c. an anti-microbial agent at 0.01-2% (w/w),
  d. an anti-inflammatory agent at 0.01-5% (w/w),
  e. a skin conditioning agent at 0.01-5% (w/w) and
  f. water to make up 100% by weight.
wherein the topical cannabinoid composition comprises less than 20% (w/w) of simple polyol.

In an embodiment of the topical cannabinoid composition as described herein, the topical cannabinoid composition comprises no more than 10% (w/w) of simple polyol.

In an embodiment of the topical cannabinoid composition as described herein, the topical cannabinoid composition comprises no more than 2% (w/w) of simple polyol.

In another aspect, there is provided a topical cannabinoid composition comprising:
  a. a cannabinoid at 0.1-10% (w/w),
  b. an antioxidant at 0.01-5% (w/w),
  c. an anti-microbial agent at 0.01-2% (w/w),
  d. an anti-inflammatory agent at 0.01-5% (w/w),
  e. a skin conditioning agent at 0.01-5% (w/w) and
  f. water at no less than 51% (w/w).

In an embodiment of the topical cannabinoid composition as described herein, the antioxidant is rosemary essential oil, the anti-microbial agent is tea tree oil, the anti-inflammatory agent is beta-caryophyllene and the skin conditioning agent is hemp seed oil.

In an embodiment of the topical cannabinoid composition as described herein, the cannabinoid is tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigervarin (CBGV), cannabigerol monomethyl ether (CBGM), cannabielsoin (CBE), cannabicitran (CBT), or any combination thereof.

In an embodiment of the topical cannabinoid composition as described herein, the cannabinoid is cannabidiol (CBD).

In an embodiment of the topical cannabinoid composition as described herein, the composition further comprises a fragrance agent at 0.01-2% (w/w) to mask the unpleasant smell of other ingredients.

In an embodiment of the topical cannabinoid composition as described herein, the fragrance agent is peppermint essential oil.

In an embodiment of the topical cannabinoid composition as described herein, the composition has a pH of 5-7.

In an embodiment of the topical cannabinoid composition as described herein, the composition further comprises one or more of:
  a. a humectant at 1-10% (w/w),
  b. a thickening agent at 0.01-10% (w/w),
  c. a gel-forming agent at 0.1-5% (w/w),
  d. a preservative at 0.1-3% (w/w),
  e. an emollient at 1-3% (w/w),
  f. a surfactant at 1-15% (w/w),
  g. a penetration enhancer at 1-5% (w/w),
  h. a pH adjusting agent in a quantity sufficient for the composition to maintain a pH of 5-7, and
  i. water to make up 100% by weight.

In an embodiment of the topical cannabinoid composition as described herein, the humectant is glycerin, the thickening agent is xanthan gum, the gel-forming agent is Carbopol 980, the preservative is phenoxyethanol, the emollient is isopropyl myristate, the surfactant is Polysorbate 80, the penetration enhancer is diethylene glycol monoethyl ether, and the pH adjusting agent is sodium hydroxide.

In an embodiment of the topical cannabinoid composition as described herein, the composition is a cream, ointment, gel, lotion, liquid, solution, spray, aerosol, any other dosage forms suitable for topical application, or any combination thereof.

In an embodiment of the topical cannabinoid composition as described herein, the composition is a gel.

In another aspect, there is provided a gel comprising:
a. a cannabinoid at 0.1-10% (w/w),
b. a gel-forming agent at 0.1-5% (w/w), and
c. water to make up 100% by weight.

In an embodiment of the gel as described herein, the composition has a viscosity in a range of about 5,000 cps to about 100,000 cps.

In another aspect, there is provided a method comprising applying the topical cannabinoid composition as described herein to the skin of a subject.

In an embodiment of the method described herein, the skin of the subject is affected by a skin disease or condition.

In an embodiment of the method as described herein, the skin disease or condition is: acne vulgaris, acne conglobata, keloid acne of the neck, recurrent miliary acne, necrotic acne, acne neonatorum, professional acne, rosacea acne, senile acne, solar acne, medication acne, skin prone to acne, erythema, fine lines, wrinkles, scarring, photoaging, loss of water, loss of elasticity, increased sagging, increased oiliness, loss of firmness, loss of color evenness or tone, coarse surface texture, and mottled pigmentation.

In another aspect, there is provided use of the topical cannabinoid composition described herein for the treatment of a skin disease or condition in a subject.

In an embodiment of the use as described herein, the skin disease or condition is acne vulgaris, acne conglobata, keloid acne of the neck, recurrent miliary acne, necrotic acne, acne neonatorum, professional acne, rosacea acne, senile acne, solar acne, medication acne, skin prone to acne, erythema, fine lines, wrinkles, scarring, photoaging, loss of water, loss of elasticity, increased sagging, increased oiliness, loss of firmness, loss of color evenness or tone, coarse surface texture, and mottled pigmentation.

Other aspects, features, and embodiments of the present disclosure will become apparent to those of ordinary skill in the art upon review of the following description of specific embodiments.

DETAILED DESCRIPTION

There is provided herein a topical cannabinoid composition useful for skin protection or for enhancing the appearance of skin. In another aspect, the composition can be used as a cleanser to remove dirt, oil, grease, tars, etc. from skin surfaces.

Composition provided herein may be useful for treating and preventing skin diseases and conditions including, but not limited to, acne, wrinkles, rosacea and erythema. Composition provided herein may also be useful for hydrating dry skin. In another aspect, the composition not only has skin cleansing effect, but it also has antioxidant, anti-inflammatory and anti-microbial properties.

Composition provided herein can also be used in conjunction with available treatments of skin diseases. Composition can also be used for routine cosmetic purposes for the prevention of skin diseases like acne and erythema.

Topical cannabinoid composition provided herein exhibit excellent overall stability and viscosity.

"Cannabinoid," as used herein, is meant to include compounds which interact with the cannabinoid receptor and various cannabinoid mimetics, such as tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigervarin (CBGV), cannabigerol monomethyl ether (CBGM), cannabielsoin (CBE) and cannabicitran (CBT).

The terms "topical composition" or "topical formulation", as used herein, means a composition in which an active agent may be placed for direct application to a skin surface and from which a therapeutically effective amount of the active agent may be released. Such formulations may include creams, ointments, gels, lotions, or any other dosage form suitable for topical application.

The terms "skin" or "skin surface" is meant to include the outer skin of a subject comprising one or more epidermal layers.

As used herein, the term "gel" means a jelly-like material that can have properties ranging from soft to hard and tough fluid. Gels can be in a liquid, a semi-liquid, a semi-solid or a solid state. Solid gels are defined as a substantially diluted cross-linked system, which exhibits no flow when in the steady state. By weight, gels are mostly liquid, yet they behave like semi-solids due to a three-dimensional cross-linked network of a solidifying, gelling or thickening agent within the liquid.

The term "active agent" is generally understood to mean an active pharmaceutical ingredient.

The terms "therapeutically effective amount" or "therapeutically and/or prophylactically effective amount" or "efficacy" as used herein, refers to an amount of compound or agent that is sufficient to elicit the required or desired therapeutic and/or prophylactic response, as the particular treatment context may require. It will be understood that a therapeutically and/or prophylactically effective amount of an active agent for a subject is dependent inter alia on the body weight of the subject as well as other factors known to a person of ordinary skill in the art.

The term "excipient" or "ingredient" herein means any substance, not itself an active agent, which may be used as a carrier or vehicle for delivery of an active agent to a subject or combined with an active agent to improve its handling or storage properties or to permit or facilitate formation of a dose unit of the composition. Examples of excipients include, but are not limited to, a "humectant", which is capable of attracting or retaining moisture; a "thickening agent", which is capable of increasing the viscosity of a composition; a "gel-forming agent", which is capable of forming a semi-crystalline structure by reaction with another material or by lowering of the temperature thereof while dissolved or colloidally suspended in a liquid medium; a "preservative", which prevents decomposition of composition by microbial growth or by undesirable chemical changes; an "emollient", which is capable of softening and soothing of the skin; a "surfactant", which act as solubilizing agent by lowering the surface tension (or interfacial tension) between two liquids or between a liquid and a solid; a "penetration enhancer", which is capable of improving penetration of an active agent into the epidermis; a "fragrance agent", also known as odorant is an aroma compound which gives a smell or odor to the composition; a "pH adjusting agent/buffering agent", which is capable of adjusting the pH (acidity or alkalinity) of the composition.

As used herein, the term "anti-oxidant" refers to a substance that inhibits oxidation or reactions promoted by oxygen or peroxides.

The term "anti-inflammatory agent" refers to a substance that directly or indirectly reduces inflammation in a tissue.

As used herein, the term "anti-microbial agent" refers to, but is not limited to, those agents that are useful in avoiding, preventing and/or treating bacterial, fungal and/or microbial infections by releasing certain substances (aka anti-bacterial, anti-fungal and/or anti-bacterial substances) that are effective at suppressing the growth of such organisms.

The term "skin conditioning agent" refers to an agent that can maintain the skin in a good condition.

The term "skin hydration" refers to the amount of water in the stratum corneum, the outermost layer of the skin, and is often used as one of the measurements of skin health. General characteristics of healthy skin include a gradual increase in the water concentration of the stratum corneum. Dehydrated skin is often associated with poor barrier function, often resulting in reduced protection against disease causing organisms, toxins, and the environment.

"wt %" or "w/w %" when referring to the percentage of a component in a composition is percentage of the weight of the component in the composition relative to the total weight of the composition.

As used herein, the terms "stable" or "stability", when referring to a composition, means that the composition can be cycled weekly between freezer and ambient room temperature conditions for a minimum of 1 month while retaining its pH and viscosity within defined ranges.

The term "viscosity" as used herein refers to the measure of the extent to which a fluid or an aqueous composition resists a force tending to cause it to flow.

The terms "treat," "treating," or "treatment of" are used herein in their broad senses unless otherwise specifically indicated in the particular context, and results of a treatment may generally include reversing, alleviating, or inhibiting the progress of an indicated disorder or condition, or one or more symptoms of the disorder or condition.

The term "prevention", as used herein, refers to the ability of a substance or composition to prevent, delay or hinder the appearance or development of a disease, disorder, condition or change before its appearance.

"Alleviate" as used herein, is meant to include complete elimination as well as any clinically or quantitatively measurable reduction in the subject's symptoms and/or discomfort.

A "subject" herein to which a therapeutic agent or composition thereof can be administered includes mammals such as a human subject of either sex and of any age, and also includes any nonhuman animal, particularly a domestic or companion animal such as a cat, dog or horse, as well as laboratory animals such as guinea pigs.

As discussed in greater detail in the illustrative and non-limiting examples provided herein, the present disclosure is directed to topical formulations/compositions that incorporate at least one cannabinoid.

In one aspect, there is provided a topical cannabinoid composition comprising:
  a. a cannabinoid at 0.1-10% (w/w),
  b. an antioxidant at 0.01-5% (w/w),
  c. an anti-microbial agent at 0.01-2% (w/w),
  d. an anti-inflammatory agent at 0.01-5% (w/w),
  e. a skin conditioning agent at 0.01-5% (w/w) and
  f. water to make up 100% by weight.
wherein the topical cannabinoid composition comprises less than 20% (w/w) of simple polyol. As used herein, the term "polyol" means an organic molecule comprising in its chemical structure at least two hydroxy moieties, such as glycerol and glycols, and derivatives thereof. As used herein, a concentration of a component referred herein is a total concentration when a topical cannabinoid composition provided herein comprises two or more compounds that are considered to belong to the same component (e.g., for a topical cannabinoid composition comprising a mixture of tetrahydrocannabinol and cannabidiol, both cannabinoids, 5% (w/w) of a cannabinoid is the total concentration of the mixture of tetrahydrocannabinol and cannabidiol).

In certain exemplary, non-limiting embodiments, a topical cannabinoid composition provided herein comprises less than 15%, less than 10%, less than 5%, less than 1%, less than 0.5%, or less than 0.1% (w/w) of simple polyol.

In another aspect, there is provided a topical cannabinoid composition comprising:
  a. a cannabinoid at 0.1-10% (w/w),
  b. an antioxidant at 0.01-5% (w/w),
  c. an anti-microbial agent at 0.01-2% (w/w),
  d. an anti-inflammatory agent at 0.01-5% (w/w),
  e. a skin conditioning agent at 0.01-5% (w/w) and
  f. water at no less than 51% (w/w).

In certain exemplary, non-limiting embodiments, a topical cannabinoid composition provided herein comprises water at no less than 55% (w/w), 60% (w/w), 65% (w/w), 70% (w/w), 75% (w/w), 80% (w/w), 85% (w/w), 90% (w/w), 91% (w/w), 92% (w/w), 93% (w/w), 94% (w/w), 95% (w/w), 96% (w/w), 97% (w/w), or 98% (w/w).

In another aspect, there is provided a gel comprising:
  a. a cannabinoid at 0.1-10% (w/w),
  b. a gel-forming agent at 0.1-5% (w/w), and
  c. water to make up 100% by weight, Exemplary cannabinoids include tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigervarin (CBGV), cannabigerol monomethyl ether (CBGM), cannabielsoin (CBE), cannabicitran (CBT), combinations, and mixtures thereof extracted from *Cannabis* plant species including *Cannabis sativa, Cannabis indica* and *Cannabis ruderalis* and all resins, stalks, flowers, seeds and oils related thereto.

In certain exemplary, non-limiting embodiments, a topical cannabinoid composition provided herein may include about 0.1% to about 10% (w/w) of cannabinoid(s). For example, a topical cannabinoid composition provided herein may comprise about 0.1% to about 10%, about 0.5% to about 10%, about 1% to about 10%, about 2% to about 10%, about 3% to about 10%, about 4% to about 10%, about 5% to about 10%, about 6% to about 10%, about 7% to about 10%, about 8% to about 10%, about 9% to about 10%, about 0.1% to about 9%, about 0.5% to about 9%, about 1% to about 9%, about 2% to about 9%, about 3% to about 9%, about 4% to about 9%, about 5% to about 9%, about 6% to about 9%, about 7% to about 9%, about 8% to about 9%, about 0.1% to about 8%, about 0.5% to about 8%, about 1% to about 8%, about 2% to about 8%, about 3% to about 8%, about 4% to about 8%, about 5% to about 8%, about 6% to about 8%, about 7% to about 8%, about 0.1% to about 7%, about 0.5% to about 7%, about 1% to about 7%, about 2% to about 7%, about 3% to about 7%, about 4% to about 7%, about 5% to about 7%, about 6% to about 7%, about 0.1% to about 6%, about 0.5% to about 6%, about 1% to about 6%, about 2% to about 6%, about 3% to about 6%, about 4% to about 6%, about 5% to about 6%, about 0.1% to about 5%, about 0.5% to about 5%, about 1% to about 5%, about 2% to about 5%, about 3% to about 5%, about 4% to about 5%, about 0.1% to about 4%, about 0.5% to about 4%, about 1% to about 4%, about 2% to about 4%, about 3% to about 4%, about 0.1% to about 3%, about 0.5% to about 3%, about 1% to about 3%, about 2% to about 3%, about 0.1% to about 2%, about 0.5% to about 2%, about 1% to about 2%, about 0.1% to about 1%, or about 0.5% to about 1% (w/w) of cannabinoid(s).

In certain exemplary, non-limiting embodiments, a topical cannabinoid composition provided herein may comprise at least 0.1%, at least 0.5%, at least 1%, at least 2%, at least 3%, at least 4%, at least 5% (w/w), at least 6% (w/w), at least 7% (w/w), at least 8% (w/w), at least 9% (w/w) or at least 10% (w/w) of cannabinoid(s).

In certain exemplary, non-limiting embodiments, a topical cannabinoid composition provided herein may comprise about 0.1%, about 0.5%, about 1%, about 2%, about 3%, about 4%, about 5%, about 6%, about 7%, about 8%, about 9% or about 10% (w/w) of cannabinoid(s).

In certain exemplary, non-limiting embodiments, topical cannabinoid compositions provided herein may be provided as creams, ointments, gels, liquids, lotions, solutions, sprays, aerosols, or combinations thereof.

In certain exemplary, non-limiting embodiments, a topical cannabinoid composition provided herein may have a viscosity in a range of about 5,000 to about 100,000 cps.

In certain exemplary, non-limiting embodiments, topical cannabinoid composition provided herein may be provided as gel. Gels offer ease of application, least irritation to the skin and optimal viscosity (e.g., in a range of about 5,000 to about 100,000 cps, about 10,000 to about 100,000 cps, about 20,000 to about 100,000 cps, about 30,000 to about 100,000 cps, about 40,000 to about 100,000 cps, about 50,000 to about 100,000 cps, about 60,000 to about 100,000 cps or about 70,000 to about 100,000 cps) that is needed for therapeutic action of cannabinoids on the epidermis of the skin, thereby providing beneficial effects on the impacted tissue or the tissue of interest for amelioration of skin disease conditions.

In certain exemplary, non-limiting embodiments, topical cannabinoid composition may include cannabinoids in a specific therapeutic amount for treating subjects with acne vulgaris, acne conglobata, keloid acne of the neck, recurrent miliary acne, necrotic acne, acne neonatorum, professional acne, rosacea acne, senile acne, solar acne, medication acne, skin prone to acne, erythema, fine lines, wrinkles, scarring, photoaging, loss of water, loss of elasticity, increased sagging, increased oiliness, loss of firmness, loss of color evenness or tone, coarse surface texture, and mottled pigmentation.

Other ingredients may be provided in topical cannabinoid composition provided herein, so long as they are physiologically acceptable and suitable for use in combination with cannabinoids.

In certain exemplary, non-limiting embodiments, a topical cannabinoid composition provided herein may include one or more antioxidant(s) and one or more anti-microbial agent(s), which may be essential oils. Examples of essential oils include anise oil, angelica oil, basil oil, bay oil, bergamot oil, rose oil, camphor oil, cardamom oil, caraway oil, cedar oil, cedarwood oil, chamomile oil, cinnamon oil, citronella oil, clove oil, copaiba balsam oil, cumin oil, coriander oil, dill oil, eucalyptus oil, fennel oil, garlic oil, geranium oil, grapefruit oil, ginger oil, guaiac oil, iris oil, Japanese mint oil, jasmine oil, lavender oil, lemon oil, lemongrass oil, lindera oil, mandarin oil, mint oil, neroli oil, onion oil, orange oil, oregano oil, patchouli oil, parsley oil, pepper oil, peppermint oil, perilla oil, Peru balsam oil, petitgrain oil, pine oil, pine needle oil, rose oil, rosemary oil, sandalwood oil, spearmint oil, star anis oil, sweet orange oil, tangerine oil, tea seed oil, tea tree oil, thyme oil, tolu balsam oil, tuberose oil, turmeric oil, western mint oil, wintergreen oil, combinations, and mixtures thereof.

In certain exemplary, non-limiting embodiments, a topical cannabinoid composition provided herein may include about 0.01% to about 5% (w/w) of antioxidant(s). For example, a topical cannabinoid composition provided herein may comprise about 0.01% to about 5%, about 0.1% to about 5%, about 0.5% to about 5%, about 1% to about 5%, about 2% to about 5%, about 3% to about 5%, about 4% to about 5%, about 0.01% to about 4%, about 0.1% to about 4%, about 0.5% to about 4%, about 1% to about 4%, about 2% to about 4%, about 3% to about 4%, about 0.01% to about 3%, about 0.1% to about 3%, about 0.5% to about 3%, about 1% to about 3%, about 2% to about 3%, about 0.01% to about 2%, about 0.1% to about 2%, about 0.5% to about 2%, about 1% to about 2%, about 0.01% to about 1%, about 0.1% to about 1% or about 0.5% to about 1% (w/w) of antioxidant(s).

In certain exemplary, non-limiting embodiments, a topical cannabinoid composition provided herein may comprise at least 0.01%, at least 0.1%, at least 0.5%, at least 1%, at least 2%, at least 3%, at least 4% or at least 5% (w/w) of antioxidant(s).

In certain exemplary, non-limiting embodiments, a topical cannabinoid composition provided herein may comprise about 0.01%, about 0.1%, about 0.5%, about 1%, about 2%, about 3%, about 4% or about 5% (w/w) of antioxidant(s).

In certain exemplary, non-limiting embodiments, a topical cannabinoid composition provided herein may include about 0.01% to about 2% (w/w) of anti-microbial agent(s). For example, a topical cannabinoid composition provided herein may comprise about 0.01% to about 2%, about 0.05% to about 2%, about 0.1% to about 2%, about 0.5% to about 2%, about 1% to about 2%, about 1.5% to about 2%, about 0.01% to about 1.5%, about 0.05% to about 1.5%, about 0.1% to about 1.5%, about 0.5% to about 1.5%, about 1% to about 1.5%, about 0.01% to about 1%, about 0.05% to about 1%, about 0.1% to about 1%, about 0.5% to about 1%, about 0.01% to about 0.5%, about 0.05% to about 0.5%, about 0.1% to about 0.5% or about 0.01% to about 0.1% (w/w) of anti-microbial agent(s).

In certain exemplary, non-limiting embodiments, a topical cannabinoid composition provided herein may comprise at least 0.01%, at least 0.05%, at least 0.1%, at least 0.5%, at least 1%, at least 1.5% or at least 2% (w/w) of anti-microbial agent(s).

In certain exemplary, non-limiting embodiments, a topical cannabinoid composition provided herein may comprise about 0.01%, about 0.05%, about 0.1%, about 0.5%, about 1%, about 1.5% or about 2% (w/w) of anti-microbial agent(s).

In certain exemplary, non-limiting embodiments, a topical cannabinoid composition provided herein may include one or more anti-inflammatory agent(s), which may be a terpene. Examples of terpenes include alpha-bisabolol, borneol, camphene, camphor, beta-caryophyllene (BCP), delta-3-carene, caryophyllene oxide, alpha-cedrene, beta-eudesmol, fenchol, geraniol (GER), guaiol, alpha-humulene, isoborneol, limonene (LIM), linalool (LIN), menthol, myrcene (MYR), neral, nerolidol (NDL), cis-ocimene, trans-ocimene, alpha-phellandrene, alpha-pinene (API), beta-pinene, sabinene, alpha terpinene, alpha-terpineol, terpinolene, alpha-guaiene, elemene, farnesene, farnesol (FOL), germacrene B, guaia-1(10), 11-diene, trans-2-pinanol, selina-3,7(11)-diene, eudesm-7(11)-en-4-ol, valencene, combinations, and mixtures thereof.

In certain exemplary, non-limiting embodiments, a topical cannabinoid composition provided herein may include about 0.01% to about 5% (w/w) of anti-inflammatory agent(s). For example, a topical cannabinoid composition provided herein may comprise about 0.01% to about 5%, about 0.1% to about 5%, about 0.5% to about 5%, about 1% to about 5%, about 2% to about 5%, about 3% to about 5%, about 4% to about 5%, about 0.01% to about 4%, about 0.1% to about 4%, about 0.5% to about 4%, about 1% to about 4%, about 2% to about 4%, about 3% to about 4%, about 0.01% to about 3%, about 0.1% to about 3%, about 0.5% to about 3%, about 1% to about 3%, about 2% to about 3%, about 0.01% to about 2%, about 0.1% to about 2%, about 0.5% to about 2%, about 1% to about 2%, about 0.01% to about 1%, about 0.1% to about 1% or about 0.5% to about 1% (w/w) of anti-inflammatory agent(s).

In certain exemplary, non-limiting embodiments, a topical cannabinoid composition provided herein may comprise at least 0.01%, at least 0.1%, at least 0.5%, at least 1%, at least 2%, at least 3%, at least 4% or at least 5% (w/w) of anti-inflammatory agent(s).

In certain exemplary, non-limiting embodiments, a topical cannabinoid composition provided herein may comprise about 0.01%, about 0.1%, about 0.5%, about 1%, about 2%, about 3%, about 4% or about 5% (w/w) of anti-inflammatory agent(s).

In certain exemplary, non-limiting embodiments, a topical cannabinoid composition provided herein may include one or more skin conditioning agent(s), which may be a vegetable oil. Examples of vegetable oils include avocado oil, canola oil, coconut oil, corn oil, cotton seed oil, flax seed oil, grape seed oil, hemp seed oil, olive oil, palm oil, peanut oil, safflower oil, soybean oil, combinations, and mixtures thereof.

In certain exemplary, non-limiting embodiments, a topical cannabinoid composition provided herein may include about 0.01% to about 5% (w/w) of skin conditioning agent(s). For example, a topical cannabinoid composition provided herein may comprise about 0.01% to about 5%, about 0.1% to about 5%, about 0.5% to about 5%, about 1% to about 5%, about 2% to about 5%, about 3% to about 5%, about 4% to about 5%, about 0.01% to about 4%, about 0.1% to about 4%, about 0.5% to about 4%, about 1% to about 4%, about 2% to about 4%, about 3% to about 4%, about 0.01% to about 3%, about 0.1% to about 3%, about 0.5% to about 3%, about 1% to about 3%, about 2% to about 3%, about 0.01% to about 2%, about 0.1% to about 2%, about 0.5% to about 2%, about 1% to about 2%, about 0.01% to about 1%, about 0.1% to about 1% or about 0.5% to about 1% (w/w) of skin conditioning agent(s).

In certain exemplary, non-limiting embodiments, a topical cannabinoid composition provided herein may comprise at least 0.01%, at least 0.1%, at least 0.5%, at least 1%, at least 2%, at least 3%, at least 4% or at least 5% (w/w) of skin conditioning agent(s).

In certain exemplary, non-limiting embodiments, a topical cannabinoid composition provided herein may comprise about 0.01%, about 0.1%, about 0.5%, about 1%, about 2%, about 3%, about 4% or about 5% (w/w) of skin conditioning agent(s).

In certain exemplary, non-limiting embodiments, a topical cannabinoid composition provided herein may include one or more humectant(s), which may be a polyol. Examples of humectants include glycerin, propylene glycol, butylene glycol, dipropylene glycol, pentylene glycol, hexylene glycol, polyethylene glycol, combinations, and mixtures thereof.

In certain exemplary, non-limiting embodiments, a topical cannabinoid composition provided herein may include about 1% to about 10% (w/w) of humectant(s). For example, a topical cannabinoid composition provided herein may comprise about 1% to about 10%, about 2% to about 10%, about 3% to about 10%, about 4% to about 10%, about 5% to about 10%, about 6% to about 10%, about 7% to about 10%, about 8% to about 10%, about 9% to about 10%, about 1% to about 9%, about 2% to about 9%, about 3% to about 9%, about 4% to about 9%, about 5% to about 9%, about 6% to about 9%, about 7% to about 9%, about 8% to about 9%, about 1% to about 8%, about 2% to about 8%, about 3% to about 8%, about 4% to about 8%, about 5% to about 8%, about 6% to about 8%, about 7% to about 8%, about 1% to about 7%, about 2% to about 7%, about 3% to about 7%, about 4% to about 7%, about 5% to about 7%, about 6% to about 7%, about 1% to about 6%, about 2% to about 6%, about 3% to about 6%, about 4% to about 6%, about 5% to about 6%, about 1% to about 5%, about 2% to about 5%, about 3% to about 5%, about 4% to about 5%, about 1% to about 4%, about 2% to about 4%, about 3% to about 4%, about 1% to about 3%, about 2% to about 3%, about 0.01% to about 2%, about 0.1% to about 2%, about 0.5% to about 2%, about 1% to about 2%, about 0.1% to about 1%, or about 0.5% to about 1% (w/w) of humectant(s).

In certain exemplary, non-limiting embodiments, a topical cannabinoid composition provided herein may comprise at least 1%, at least 2%, at least 3%, at least 4%, at least 5%, at least 6%, at least 7%, at least 8%, at least 9%, or at least 10% (w/w) of humectant(s).

In certain exemplary, non-limiting embodiments, a topical cannabinoid composition provided herein may comprise about 1%, about 2%, about 3%, about 4%, about 5%, about 6%, about 7%, about 8%, about 9%, or about 10% (w/w) of humectant(s).

In certain exemplary, non-limiting embodiments, a topical cannabinoid composition provided herein may include one or more thickening agent(s), which may be a gum. Examples of gums include acacia, agar, alginic acid, ammonium alginate, amylopectin, calcium alginate, calcium carrageenan, carrageenan, dextrin, gelatin, gellan gum, guar gum, hydroxypropyl guar, guar hydroxypropyltrimonium chloride, hydroxypropyl guar hydroxypropyltrimonium chloride, karaya gum, locust bean gum, natto gum, potassium alginate, potassium carrageenan, propylene glycol alginate, *sclerotium* gum, sodium carboyxmethyl dextran, sodium carrageenan, tragacanth gum, xanthan gum, combinations, and mixtures thereof.

In certain exemplary, non-limiting embodiments, a topical cannabinoid composition provided herein may include about 0.1% to about 10% (w/w) of thickening agent(s).

In certain exemplary, non-limiting embodiments, a topical cannabinoid composition provided herein may comprise about 0.1%, about 0.5%, about 1%, about 2%, about 3%, about 4%, about 5%, about 6%, about 7%, about 8%, about 9%, or about 10% (w/w) of thickening agent(s).

In certain exemplary, non-limiting embodiments, a topical cannabinoid composition provided herein may include one or more gel-forming agent(s) selected from the group consisting of the family of polyacrylamides; copolymers of acrylic acid; "electrolyte-insensitive" carbomers; polysaccharides; cellulose and derivatives thereof; and magnesium aluminum silicates. Examples include sodium acryloyldimethyltaurate copolymer/isohexadecane/polysorbate 80 mixture, the polyacrylamide/C13-14 isoparaffin/laureth-7 mixture, Carbopol 1382, Carbopol 980, Pemulen™ TR, xanthan gum, hydroxypropylmethylcellulose or hydroxyethylcellulose, combinations, and mixtures thereof.

In certain exemplary, non-limiting embodiments, a topical cannabinoid composition provided herein may include about 0.1% to about 5% (w/w) of gel-forming agent(s).

In certain exemplary, non-limiting embodiments, a topical cannabinoid composition provided herein may comprise about 0.1%, about 0.5%, about 1%, about 2%, about 3%, about 4%, or about 5% (w/w) of gel-forming agent(s).

In certain exemplary, non-limiting embodiments, a topical cannabinoid composition provided herein may include one or more preservative(s), such as ethyl paraben, methylparaben, propylparaben, butylparaben, isobutyl paraben, benzalkonium chloride, imidurea, phenoxyethanol, ethylenediaminetetraacetic acid (EDTA), combinations, and mixtures thereof.

In certain exemplary, non-limiting embodiments, a topical cannabinoid composition provided herein may include about 0.1% to about 3% (w/w) of preservative(s).

In certain exemplary, non-limiting embodiments, a topical cannabinoid composition provided herein may comprise about 0.1%, about 0.5%, about 1%, about 2%, or about 3% (w/w) of preservative(s).

In certain exemplary, non-limiting embodiments, a topical cannabinoid composition provided herein may include one or more emollient(s), which may be a liquid fatty acid ester. Examples of liquid fatty acid esters include cetyl octanoate, glyceryl trioctanoate, isopropyl linoleate, isopropyl myristate, isopropyl oleate, ethyllaurate, ethyl linoleate, octyl dodecyl myristate, octyl palmitate, octyl isopelargonate, octyl dodecyllactate, isotridecyl isononanoate, oleyl oleate, isostearyl myristate, neopentyl glycol dioctanoate, di(capryl/capric acid) propylene glycol, combinations, and mixtures thereof.

In certain exemplary, non-limiting embodiments, a topical cannabinoid composition provided herein may include about 1% to about 3% (w/w) of emollient(s).

In certain exemplary, non-limiting embodiments, a topical cannabinoid composition provided herein may comprise about 1%, about 2%, or about 3% (w/w) of emollient(s).

In certain exemplary, non-limiting embodiments, a topical cannabinoid composition provided herein may include one or more surfactant(s), which may be a non-ionic surfactant. Examples of non-ionic surfactants include polysorbate 20 (Tween 20), polysorbate 40 (Tween 40), polysorbate 60 (Tween 60), polysorbate 80 (Tween 80), combinations, and mixtures thereof.

In certain exemplary, non-limiting embodiments, a topical cannabinoid composition provided herein may include about 1% to about 15% (w/w) of surfactant(s).

In certain exemplary, non-limiting embodiments, a topical cannabinoid composition provided herein may comprise about 1%, about 2%, about 3%, about 4%, about 5%, about 6%, about 7%, about 8%, about 9%, about 10%, about 11%, about 12%, about 13%, about 14%, or about 15% (w/w) of surfactant(s).

In certain exemplary, non-limiting embodiments, a topical cannabinoid composition provided herein may include one or more penetration enhancer(s) which may be a glycol ether, unsaturated fatty acid or alcohol. Examples include diethylene glycol monoethyl ether, steareth-20, steareth-2, octyl decanol, isopropyl myristate, oleic acid, propylene glycol combinations, and mixtures thereof.

In certain exemplary, non-limiting embodiments, a topical cannabinoid composition provided herein may include about 1% to about 5% (w/w) of penetration enhancer(s).

In certain exemplary, non-limiting embodiments, a topical cannabinoid composition provided herein may comprise about 1%, about 2%, about 3%, about 4%, or about 5% (w/w) of penetration enhancer(s).

In certain exemplary, non-limiting embodiments, a topical cannabinoid composition provided herein may include one or more fragrance agent(s) selected from the group consisting of carvone oil, geranium oil, ho wood oil, jasmine oil, lavodin oil, limonene oil, nerolina oil, peppermint oil, terpineol, vetiver, combinations, and mixtures thereof.

In certain exemplary, non-limiting embodiments, a topical cannabinoid composition provided herein may include about 0.01% to about 2% (w/w) of fragrance agent(s).

In certain exemplary, non-limiting embodiments, a topical cannabinoid composition provided herein may comprise about 0.01%, about 0.05%, about 0.1%, about 1%, about 1.5% or about 2% (w/w) of fragrance agent(s).

In certain exemplary, non-limiting embodiments, a topical cannabinoid composition provided herein may include one or more pH adjusting agent(s)/buffering agent(s), such as calcium hydroxide, sodium hydroxide, potassium hydroxide, citrate/citric acid, acetate/acetic acid, phosphate/phosphoric acid, formate/formic acid, propionate/propionic acid, lactate/lactic acid, carbonate/carbonic acid, ammonium/ammonia buffer, triethylamine, triethanolamine, combinations, and mixtures thereof. In certain exemplary, non-limiting embodiments, the composition may have a pH within the range of about 5 to about 7.

In certain exemplary, non-limiting embodiments, a topical cannabinoid composition provided herein may include one or more carriers, such as water, alcohol, mineral oil, combinations, and mixtures thereof.

In certain exemplary, non-limiting embodiments, a topical cannabinoid composition provided herein may retain a viscosity in a range of about 5,000 to about 100,000 cps and a pH within a range of about 5 to about 7 while being cycled weekly between freezer and ambient room temperature conditions for a minimum of 3 months.

It is understood that the amount of cannabinoid necessary to achieve a desired therapeutic result is influenced by, and will therefore vary based on, a number of factors, including for example and without limitation, the age, sex, and weight of the subject, factors that influence the metabolic rate, and the specific disorders, diseases or related treatment symptoms of the subject. The concentration of at least one cannabinoid in compositions provided herein is between about 0.002% and about 10%.

One of skill in the art will understand that the ingredients in the final formulations must total 100% and, based on the teachings provided herein, will understand that modifications to the exemplary formulations provided herein are possible (e.g., replacement of a recited ingredient with a different ingredient, addition of a different ingredient, and/or modification of an amount of an ingredient) provided that such modifications result in a formulation as taught and described herein (i.e., capable of delivering an active agent such as a cannabinoid topically).

In another aspect, there is provided a method of applying a topical cannabinoid composition provided herein to the skin of a subject. In some embodiments, the skin is affected by a skin disease or condition. Application may be carried out by dropping, spraying, diffusing, dispersing, squirting, or spreading the composition, and may optionally be carried out using an applicator, such as a dropper, a nebulizer, an impregnated gauze sheet, a syringe, or a cotton swab.

In another aspect, there is provided a method of treating a skin disease or condition in a subject, comprising applying a topical cannabinoid composition provided herein to the skin of a subject.

In another aspect, there is provided a use of a topical cannabinoid composition provided herein for the treatment of a skin disease or condition in a subject.

In certain exemplary, non-limiting embodiments, the skin disease or condition is: acne vulgaris, acne conglobata, cheloid acne of the neck, recurrent miliary acne, necrotic acne, acne neonatorum, professional acne, rosacea acne, senile acne, solar acne, medication acne, skin prone to acne, erythema, fine lines, wrinkles, scarring, photoaging, loss of water, loss of elasticity, increased sagging, increased oiliness, loss of firmness, loss of color evenness or tone, coarse surface texture, and mottled pigmentation.

Still further embodiments of the present disclosure relate to providing a kit, which may include a container containing a topical cannabinoid composition provided herein, or a number of containers containing materials for preparing the topical cannabinoid composition. The kit may also include instructions for treating a skin disease or condition using the topical cannabinoid composition including dosage and how the composition may be applied to the skin. When separate containers are provided in the kit, and depending on the contents in these containers, the kit may also include instructions for preparing a topical cannabinoid composition, or compositions with different concentrations of active ingredients, from the materials included in the kit and optionally other materials such as a carrier or other additives. The kit may further include an applicator for applying the topical cannabinoid composition to the skin of a subject and may include specific instructions on how to use the applicator.

In certain exemplary, non-limiting embodiments, a topical cannabinoid composition provided herein may be prepared or obtained from a kit comprising (a) one or more cannabinoids; (b) ingredients; and (c) instructions in the kit, and wherein the instructions comprise information allowing all of (b) be mixed with (a) at selected concentrations disclosed herein. The kit may include separate containers or instructions for providing or preparing more than one composition with different concentrations for one or more of (a) and (b).

In certain exemplary, non-limiting embodiments, a kit may include a container containing a topical cannabinoid composition provided herein. The composition may be in form of cream, ointment, gel, liquid or the like as described above. The container may be, for example, a liquid bottle or a paste tube depending on the physical form of the composition. In other embodiments, a kit may include a plurality of containers containing materials for forming a topical cannabinoid composition provided herein. The kit may further comprise at least one of instructions for applying the composition to skin; instructions for using the composition to treat a skin disease or condition according to the methods or uses provided herein; and instructions for using the materials in the plurality of containers to prepare the composition according to the methods of preparation provided herein. Optional components of a kit may include one or more applicators (such as droppers, sprayers, gauze sheets, and cotton-tipped applicators) for applying the composition to skin. The one or more applicators may be sterilized and contained in a sealed sterile packaging.

The discussion herein and the following examples set forth and illustrate various exemplary embodiments of the present disclosure, which are understood to be illustrative and non-limiting.

Non-Limiting Embodiments

Particular embodiments of the disclosure include, without limitation, the following:

1. A topical cannabinoid composition comprising:
   a. a cannabinoid at 0.1-10% (w/w),
   b. an antioxidant at 0.01-5% (w/w),
   c. an anti-microbial agent at 0.01-2% (w/w),
   d. an anti-inflammatory agent at 0.01-5% (w/w),
   e. a skin conditioning agent at 0.01-5% (w/w) and
   f. water to make up 100% by weight.
   wherein the topical cannabinoid composition comprises less than 20% (w/w) of simple polyol.

2. The topical cannabinoid composition of embodiment 1, wherein the topical cannabinoid composition comprises less than 15% (w/w) of simple polyol.

3. The topical cannabinoid composition of embodiment 1 or 2, wherein the topical cannabinoid composition comprises less than 10% (w/w) of simple polyol.

4. The topical cannabinoid composition of embodiment 1 or 2, wherein the topical cannabinoid composition comprises less than 5% (w/w) of simple polyol.

5. A topical cannabinoid composition comprising:
   a. a cannabinoid at 0.1-10% (w/w),
   b. an antioxidant at 0.01-5% (w/w),
   c. an anti-microbial agent at 0.01-2% (w/w),
   d. an anti-inflammatory agent at 0.01-5% (w/w),
   e. a skin conditioning agent at 0.01-5% (w/w) and
   f. water at no less than 51% (w/w).

6. The topical cannabinoid composition of any one of embodiments 1 to 5, which comprises about 0.1% (w/w) of the cannabinoid.

7. The topical cannabinoid composition of any one of embodiments 1 to 5, which comprises about 0.5% (w/w) of the cannabinoid.

8. The topical cannabinoid composition of any one of embodiments 1 to 5, which comprises about 1% (w/w) of the cannabinoid.

9. The topical cannabinoid composition of any one of embodiments 1 to 5, which comprises about 2% (w/w) of the cannabinoid.

10. The topical cannabinoid composition of any one of embodiments 1 to 5, which comprises about 3% (w/w) of the cannabinoid.

11. The topical cannabinoid composition of any one of embodiments 1 to 5, which comprises about 4% (w/w) of the cannabinoid.

12. The topical cannabinoid composition of any one of embodiments 1 to 5, which comprises about 5% (w/w) of the cannabinoid.

13. The topical cannabinoid composition of any one of embodiments 1 to 5, which comprises about 6% (w/w) of the cannabinoid.

14. The topical cannabinoid composition of any one of embodiments 1 to 5, which comprises about 7% (w/w) of the cannabinoid.

15. The topical cannabinoid composition of any one of embodiments 1 to 5, which comprises about 8% (w/w) of the cannabinoid.

16. The topical cannabinoid composition of any one of embodiments 1 to 5, which comprises about 9% (w/w) of the cannabinoid.

17. The topical cannabinoid composition of any one of embodiments 1 to 5, which comprises about 10% (w/w) of the cannabinoid.

18. The topical cannabinoid composition of any one of embodiments 1 to 17, wherein the cannabinoid is tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigervarin (CBGV), cannabigerol monomethyl ether (CBGM), cannabielsoin (CBE), cannabicitran (CBT), or any combination thereof.

19. The topical cannabinoid composition of embodiment 18, wherein the cannabinoid is cannabidiol (CBD).

20. The topical cannabinoid composition of embodiments 1 to 19, which comprises about 0.01% (w/w) of the antioxidant.

21. The topical cannabinoid composition of embodiments 1 to 19, which comprises about 0.1% (w/w) of the antioxidant.

22. The topical cannabinoid composition of embodiments 1 to 19, which comprises about 0.5% (w/w) of the antioxidant.

23. The topical cannabinoid composition of embodiments 1 to 19, which comprises about 1% (w/w) of the antioxidant.

24. The topical cannabinoid composition of embodiments 1 to 19, which comprises about 2% (w/w) of the antioxidant.

25. The topical cannabinoid composition of embodiments 1 to 19, which comprises about 3% (w/w) of the antioxidant.

26. The topical cannabinoid composition of embodiments 1 to 19, which comprises about 4% (w/w) of the antioxidant.

27. The topical cannabinoid composition of embodiments 1 to 19, which comprises about 5% (w/w) of the antioxidant.

28. The topical cannabinoid composition of embodiments 1 to 19, which comprises about 0.01% (w/w) of the anti-microbial agent.

29. The topical cannabinoid composition of embodiments 1 to 19, which comprises about 0.05% (w/w) of the anti-microbial agent.

30. The topical cannabinoid composition of embodiments 1 to 19, which comprises about 0.1% (w/w) of the anti-microbial agent.

31. The topical cannabinoid composition of embodiments 1 to 19, which comprises about 0.5% (w/w) of the anti-microbial agent.

32. The topical cannabinoid composition of embodiments 1 to 19, which comprises about 1% (w/w) of the anti-microbial agent.

33. The topical cannabinoid composition of embodiments 1 to 19, which comprises about 1.5% (w/w) of the anti-microbial agent.

34. The topical cannabinoid composition of embodiments 1 to 19, which comprises about 2% (w/w) of the anti-microbial agent.

35. The topical cannabinoid composition of embodiments 1 to 34, wherein the antioxidant and anti-microbial agents are essential oils.

36. The topical cannabinoid composition of embodiment 35, wherein the essential oils are anise oil, angelica oil, basil oil, bay oil, bergamot oil, rose oil, camphor oil, cananga oil, cardamom oil, caraway oil, cedar oil, cedarwood oil, *Chamaecyparis obtusa* oil, chamomile oil, cinnamon oil, citronella oil, clove oil, copaiba balsam oil, cumin oil, coriander oil, dill oil, eucalyptus oil, fennel oil, garlic oil, geranium oil, grapefruit oil, ginger oil, guaiac oil, hiba oil, iris oil, Japanese mint oil, jasmine oil, lavender oil, lemon oil, lemongrass oil, linaloe oil, Lindera oil, mandarin oil, mint oil, neroli oil, onion oil, orange oil, oregano oil, palmarosa sofia oil, patchouli oil, parsley oil, pepper oil, peppermint oil, perilla oil, Peru balsam oil, petitgrain oil, pine oil, pine needle oil, rose oil, rosemary oil, sandalwood oil, spearmint oil, star anis oil, sweet orange oil, tangerine oil, tea seed oil, tea tree oil, thyme oil, tolu balsam oil, tuberose oil, turmeric oil, vetivert oil, western mint oil, wintergreen oil, or any combination thereof.

37. The topical cannabinoid composition of embodiment 36, wherein the antioxidant is rosemary oil.

38. The topical cannabinoid composition of embodiment 36, wherein the anti-microbial agent is tea tree oil.

39. The topical cannabinoid composition of embodiments 1 to 38, which comprises about 0.01% (w/w) of anti-inflammatory agent.

40. The topical cannabinoid composition of embodiments 1 to 38, which comprises about 0.1% (w/w) of anti-inflammatory agent.

41. The topical cannabinoid composition of embodiments 1 to 38, which comprises about 0.5% (w/w) of anti-inflammatory agent.

42. The topical cannabinoid composition of embodiments 1 to 38, which comprises about 1% (w/w) of anti-inflammatory agent.

43. The topical cannabinoid composition of embodiments 1 to 38, which comprises about 2% (w/w) of anti-inflammatory agent.

44. The topical cannabinoid composition of embodiments 1 to 38, which comprises about 3% (w/w) of anti-inflammatory agent.

45. The topical cannabinoid composition of embodiments 1 to 38, which comprises about 4% (w/w) of anti-inflammatory agent.

46. The topical cannabinoid composition of embodiments 1 to 38, which comprises about 5% (w/w) of anti-inflammatory agent.

47. The topical cannabinoid composition of embodiments 1 to 46, wherein the anti-inflammatory agent is a terpene.

48. The topical cannabinoid composition of embodiment 47, wherein the terpene is alpha-bisabolol, borneol, camphene, camphor, beta-caryophyllene (BCP), delta-3-carene, caryophyllene oxide, alpha-cedrene, beta-eudesmol, fenchol, geraniol (GER), guaiol, alpha-humulene, isoborneol, limonene (LIM), linalool (LIN), menthol, myrcene (MYR), neral, nerolidol (NDL), cis-ocimene, trans-ocimene, alpha-phellandrene, alpha-pinene (API), beta-pinene, sabinene, alpha terpinene, alpha-terpineol, terpinolene, alpha-guaiene, elemene, farnesene, farnesol (FOL), germacrene B, guaia-1(10), 11-diene, trans-2-pinanol, selina-3,7(11)-diene, eudesm-7(11)-en-4-ol, valencene, or any combination thereof.

49. The topical cannabinoid composition of embodiment 48, wherein the anti-inflammatory agent is beta-caryophyllene.

50. The topical cannabinoid composition of embodiments 1 to 48, which comprises about 0.01% (w/w) of skin conditioning agent.

51. The topical cannabinoid composition of embodiments 1 to 48, which comprises about 0.1% (w/w) of skin conditioning agent.

52. The topical cannabinoid composition of embodiments 1 to 48, which comprises about 0.5% (w/w) of skin conditioning agent.

53. The topical cannabinoid composition of embodiments 1 to 48, which comprises about 1% (w/w) of skin conditioning agent.

54. The topical cannabinoid composition of embodiments 1 to 48, which comprises about 2% (w/w) of skin conditioning agent.

55. The topical cannabinoid composition of embodiments 1 to 48, which comprises about 3% (w/w) of skin conditioning agent.

56. The topical cannabinoid composition of embodiments 1 to 48, which comprises about 4% (w/w) of skin conditioning agent.

57. The topical cannabinoid composition of embodiments 1 to 48, which comprises about 5% (w/w) of skin conditioning agent.

58. The topical cannabinoid composition of embodiments 1 to 57, wherein the skin conditioning agent is a vegetable oil.

59. The topical cannabinoid composition of embodiment 58, wherein the vegetable oil is avocado oil, canola oil, coconut oil, corn oil, cotton seed oil, flax seed oil, grape seed oil, hemp seed oil, olive oil, palm oil, peanut oil, safflower oil, soybean oil, or any combination thereof.

60. The topical cannabinoid composition of embodiment 59, wherein the vegetable oil is hemp seed oil.

61. The topical cannabinoid composition of embodiments 1 to 60, which comprises about 1% (w/w) of humectant.

62. The topical cannabinoid composition of embodiments 1 to 60, which comprises about 2% (w/w) of humectant.

63. The topical cannabinoid composition of embodiments 1 to 60, which comprises about 3% (w/w) of humectant.

64. The topical cannabinoid composition of embodiments 1 to 60, which comprises about 4% (w/w) of humectant.

65. The topical cannabinoid composition of embodiments 1 to 60, which comprises about 5% (w/w) of humectant.

66. The topical cannabinoid composition of embodiments 1 to 60, which comprises about 6% (w/w) of humectant.

67. The topical cannabinoid composition of embodiments 1 to 60, which comprises about 7% (w/w) of humectant.

68. The topical cannabinoid composition of embodiments 1 to 60, which comprises about 8% (w/w) of humectant.

69. The topical cannabinoid composition of embodiments 1 to 60, which comprises about 9% (w/w) of humectant.

70. The topical cannabinoid composition of embodiments 1 to 60, which comprises about 10% (w/w) of humectant.

71. The topical cannabinoid composition of embodiment 70, wherein the humectant is a polyol.

72. The topical cannabinoid composition of embodiment 71, wherein the polyol is glycerin, propylene glycol, butylene glycol, dipropylene glycol, pentylene glycol, hexylene glycol, polyethylene glycol, or any combination thereof.

73. The topical cannabinoid composition of embodiment 70, wherein the humectant is glycerin.

74. The topical cannabinoid composition of embodiments 1 to 73, wherein the composition further comprises a thickening agent at 0.1-10% (w/w).

75. The topical cannabinoid composition of embodiment 74, wherein the thickening agent is a gum.

76. The topical cannabinoid composition of embodiment 75, wherein the gum is acacia, agar, alginic acid, ammonium alginate, amylopectin, calcium alginate, calcium carrageenan, carrageenan, dextrin, gelatin, gellan gum, guar gum, hydroxypropyl guar, guar hydroxypropyltrimonium chloride, hydroxypropyl guar hydroxypropyltrimonium chloride, karaya gum, locust bean gum, natto gum, potassium alginate, potassium carrageenan, propylene glycol alginate, *sclerotium* gum, sodium carboyxmethyl dextran, sodium carrageenan, tragacanth gum, xanthan gum, or any combination thereof.

77. The topical cannabinoid composition of embodiment 76, wherein the thickening agent is xanthan gum.

78. The topical cannabinoid composition of embodiments 1 to 77, wherein the composition further comprises a gel-forming agent at 0.1-5% (w/w).

79. The topical cannabinoid composition of embodiment 78, wherein the gel-forming agent is sodium acryloyldimethyltaurate copolymer/isohexadecane/polysorbate 80 mixture, the polyacrylamide/C13-14 isoparaffin/laureth-7 mixture, Carbopol 1382, Carbopol 980, Pemulen™ TR, xanthan gum, hydroxypropylmethylcellulose, hydroxyethylcellulose, or any combination thereof.

80. The topical cannabinoid composition of embodiment 79, wherein the gel-forming agent is Carbopol 980.

81. The topical cannabinoid composition of embodiments 1 to 80, wherein the composition further comprises a preservative at 0.1-3% (w/w).

82. The topical cannabinoid composition of embodiment 81, wherein the preservative is ethylparaben, methylparaben, propylparaben, butylparaben, isobutylparaben, benzalkonium chloride, imidurea, phenoxyethanol, ethylenediaminetetraacetic acid (EDTA) or any combination thereof.

83. The topical cannabinoid composition of embodiment 82, wherein the preservative is phenoxyethanol.

84. The topical cannabinoid composition of embodiments 1 to 83, wherein the composition further comprises an emollient at 1-3% (w/w).

85. The topical cannabinoid composition of embodiment 84, wherein the emollient is a liquid fatty acid ester.

86. The topical cannabinoid composition of embodiment 85, wherein the liquid fatty acid ester is cetyl octanoate, glyceryl trioctanoate, isopropyl linoleate, isopropyl myristate, isopropyl oleate, ethyllaurate, ethyl linoleate, octyl dodecyl myristate, octyl palmitate, octyl isopelargonate, octyl dodecyllactate, isotridecyl isononanoate, oleyl oleate, isostearyl myristate, neopentyl glycol dioctanoate, di(capryl/capric acid) propylene glycol, or any combination thereof.

87. The topical cannabinoid composition of embodiment 86, wherein the emollient is isopropyl myristate.

88. The topical cannabinoid composition of embodiments 1 to 87, wherein the composition further comprises a surfactant at 1-15% (w/w).

89. The topical cannabinoid composition of embodiment 88, wherein the surfactant is a non-ionic surfactant.

90. The topical cannabinoid composition of embodiment 89, wherein the non-ionic surfactant is polysorbate 20 (Tween 20), polysorbate 40 (Tween 40), polysorbate 60 (Tween 60), polysorbate 80 (Tween 80), or any combination thereof.

91. The topical cannabinoid composition of embodiment 90, wherein the surfactant is polysorbate 80 (Tween 80).

92. The topical cannabinoid composition of embodiments 1 to 91, wherein the composition further comprises a penetration enhancer at 1-5% (w/w).

93. The topical cannabinoid composition of embodiment 92, wherein the penetration enhancer is a glycol ether.

94. The topical cannabinoid composition of embodiment 93, wherein the glycol ether is diethylene glycol monoethyl ether, steareth-20, steareth-2, octyldecanol, isopropyl myristate, or any combination thereof.

95. The topical cannabinoid composition of embodiment 94, wherein the penetration enhancer is diethylene glycol monoethyl ether.

96. The topical cannabinoid composition of embodiments 1 to 94, wherein the composition further comprises a fragrance agent at 0.01-2% (w/w).

97. The topical cannabinoid composition of embodiment 96, wherein the fragrance agent is carvone oil, geranium oil, ho wood oil, jasmine oil, lavodin oil, limonene oil, nerolina oil, peppermint oil, terpineol, vetiver, or any combination thereof.

98. The topical cannabinoid composition of embodiment 97, wherein the fragrance agent is peppermint oil.

99. The topical cannabinoid composition of embodiments 1 to 98, wherein the composition further comprises a pH adjusting agent/buffering agent.

100. The topical cannabinoid composition of embodiment 99, wherein the pH adjusting agent/buffering agent is calcium hydroxide, sodium hydroxide, potassium hydroxide, citrate/citric acid, acetate/acetic acid, phosphate/phosphoric acid, formate/formic acid, propionate/propionic acid, lactate/lactic acid, carbonate/carbonic acid, ammonium/ammonia buffer, triethylamine, triethanolamine or any combination thereof.

101. The topical cannabinoid composition of embodiment 100, wherein the pH adjusting agent/buffering agent is sodium hydroxide.

102. The topical cannabinoid composition of any one of embodiments 1 to 101, wherein the composition has a pH within the range of about 5 to about 7.

103. The topical cannabinoid composition of any one of embodiments 1 to 102, wherein the composition has a viscosity in a range of about 5,000 to about 100,000 cps.

104. The topical cannabinoid composition of any one of embodiments 1 to 103, wherein the composition has a viscosity in a range of about 5,000 to about 100,000 cps and a pH within a range of about 5 to about 7, and retains its viscosity and pH within the said ranges while being cycled weekly between freezer and ambient room temperature conditions for a minimum of 3 months.

105. The topical cannabinoid composition of any one of embodiments 1 to 104, wherein the composition is a cream, ointment, gel, lotion, liquid, solution, spray, aerosol, any other dosage forms suitable for topical application, or any combination thereof.

106. The topical cannabinoid composition of embodiment 105, wherein the composition is a gel.

107. A method comprising applying the topical cannabinoid composition of any one of embodiments 1 to 106 to the skin of a subject.

108. The method of embodiment 107, wherein the skin of the subject is affected by a skin disease or condition.

109. The method of embodiment 108, wherein the skin disease or condition is: acne vulgaris, acne conglobata, keloid acne of the neck, recurrent miliary acne, necrotic acne, acne neonatorum, professional acne, rosacea acne, senile acne, solar acne, medication acne, skin prone to acne, erythema, fine lines, wrinkles, scarring, photoaging, loss of water, loss of elasticity, increased sagging, increased oiliness, loss of firmness, loss of color evenness or tone, coarse surface texture, and mottled pigmentation.

110. A method of treating a skin disease or condition in a subject, comprising applying the topical cannabinoid composition of any one of embodiments 1 to 109 to the skin of a subject.

111. The method of embodiment 110, wherein the skin disease or condition is: acne vulgaris, acne conglobata, keloid acne of the neck, recurrent miliary acne, necrotic acne, acne neonatorum, professional acne, rosacea acne, senile acne, solar acne, medication acne, skin prone to acne, erythema, fine lines, wrinkles, scarring, photoaging, loss of water, loss of elasticity, increased sagging, increased oiliness, loss of firmness, loss of color evenness or tone, coarse surface texture, and mottled pigmentation.

112. The method of any one of embodiments 107 to 111, wherein the applying comprises dropping, spraying, diffusing, dispersing, squirting, or spreading the composition.

113. The method of any one of embodiments 107 to 112, wherein the subject is a mammal.

114. The method of any one of embodiments 107 to 113, wherein the subject is a companion animal.

115. The method of embodiment 113, wherein the subject is a human.

116. The method of any one of embodiments 107 to 115, wherein the method further comprises administering an additional therapy for a skin disease or condition.

117. Use of the topical cannabinoid formulation of any one of embodiments 1 to 106 for the treatment of a skin disease or condition in a subject.

118. The use of embodiment 117, wherein the skin disease or condition is: acne vulgaris, acne conglobata, keloid acne of the neck, recurrent miliary acne, necrotic acne, acne neonatorum, professional acne, rosacea acne, senile acne, solar acne, medication acne, skin prone to acne, erythema, fine lines, wrinkles, scarring, photoaging, loss of water, loss of elasticity, increased sagging, increased oiliness, loss of firmness, loss of color evenness or tone, coarse surface texture, and mottled pigmentation.

119. The use of any one of embodiments 117 or 118, wherein the subject is a mammal.

120. The use of any one of embodiments 117 to 119, wherein the subject is a companion animal.

121. The use of embodiment 119, wherein the subject is a human.

122. The use of any one of embodiments 117 to 121, wherein the treatment further comprises an additional therapy for a skin disease or condition.

123. A kit comprising a container containing the topical cannabinoid composition of any one of embodiments 1 to 106.

124. A kit comprising a plurality of containers containing materials for forming the topical cannabinoid composition of any one of embodiments 1 to 106.

125. The kit of embodiment 123 or 124, further comprising instructions for preparing the topical cannabinoid composition from the materials in the containers.

126. The kit of any one of embodiments 123 to 125, further comprising instructions for applying the topical cannabinoid composition to the skin of a subject.

127. The kit of any one of embodiments 123 to 126, further comprising instructions for using the topical cannabinoid composition to treat a skin disease or condition according to the method of any one of embodiments 107 to 115.

128. The kit of any one of embodiments 123 to 127, further comprising one or more applicators for applying the topical cannabinoid composition to the skin of a subject.

129. A topical cannabinoid composition comprising:
  a. a cannabinoid at 0.1-10% (w/w),
  b. an antioxidant at 0.01-5% (w/w),
  c. an anti-microbial agent at 0.01-2% (w/w),
  d. an anti-inflammatory agent at 0.01-5% (w/w),
  e. a skin conditioning agent at 0.01-5% (w/w),
  f. a humectant at 1-10% (w/w),
  g. a thickening agent at 0.01-10% (w/w),
  h. a gel-forming agent at 0.1-5% (w/w),
  i. a preservative at 0.1-3% (w/w),
  j. an emollient at 1-3% (w/w),
  k. a non-ionic surfactant at 1-15% (w/w).
  l. a penetration enhancer at 1-5% (w/w),
  m. a fragrance agent at 0.01-2% (w/w),
  n. a pH adjusting agent in a quantity sufficient for the composition to maintain pH 5-7, and
  o. water to make up 100% by weight.

130. The topical cannabinoid composition of embodiment 129, wherein said cannabinoid is CBD, anti-oxidant is rosemary oil, anti-microbial agent is tea tree oil, anti-inflammatory agent is beta-caryophyllene (BCP), skin conditioning agent is hemp seed oil, humectant is glycerin, thickening agent is xanthan gum, gel-forming agent is Carbopol 980, preservative is phenoxyethanol, emollient is isopropyl myristate, non-ionic surfactant is polysorbate 80, penetration enhancer is diethylene glycol monoethyl ether, fragrance agent is peppermint essential oil and pH adjusting agent is sodium hydroxide.

131. The topical cannabinoid composition of embodiment 129, wherein the said composition has a pH within the range of about 5 to 7.

132. The topical cannabinoid composition of embodiment 129, wherein the said composition has a viscosity in a range of about 5,000 to about 100,000 cps.

133. The topical cannabinoid composition of embodiment 129, wherein the said composition is a topical gel composition.

134. The topical cannabinoid composition of any one of embodiments 129 to 134, wherein the compositions are useful for the treatment of one or more skin diseases or conditions such as: acne vulgaris, acne conglobata, keloid acne of the neck, recurrent miliary acne, necrotic acne, acne neonatorum, professional acne, rosacea acne, senile acne, solar acne, medication acne, skin prone to acne, erythema, fine lines, wrinkles, scarring, photoaging, loss of water, loss of elasticity, increased sagging, increased oiliness, loss of firmness, loss of color evenness or tone, coarse surface texture, and mottled pigmentation.

135. A gel comprising:
 a. a cannabinoid at 0.1-10% (w/w),
 b. a gel-forming agent at 0.1-5% (w/w), and
 c. water to make up 100% by weight.

136. The gel of embodiment 135, wherein the composition has a viscosity in a range of about 5,000 to about 100,000 cps.

The following examples are provided to illustrate certain particular features and/or embodiments. These examples should not be construed to limit the disclosure to the particular features or embodiments described.

Non-Limiting Examples

Example 1

Topical cannabinoid composition: This example provides an overview of embodiments of the cannabinoid composition described herein, which is useful in the topical treatment of skin conditions such as acne, skin prone to acne, fatty/oily skin or of improving skin hydration.

TABLE 1

| Phase | Ingredient | INCI | w/w % |
|---|---|---|---|
| Pre-Emulsion Phase (A) | Aqua | Water | 41.45 |
| Aqueous Phase (B) | Aqua | Water | 43.95 |
| | Glycerin | Glycerin | 2 |
| | Xanthan gum | Xanthan gum | 0.2 |
| | Carbopol 980 | Carbomer | 1 |
| Oil Phase (C) | Phenoxyethanol | Phenoxyethanol | 0.5 |
| | Isopropyl myristate | Isopropyl myristate | 2 |
| | Tween 80 | Polysorbate 80 | 3 |
| | Diethylene glycol monoethyl ether | Ethoxydiglycol | 2 |
| | Rosemary oil | *Rosmarinus officinalis* leaf oil | 0.1 |

TABLE 1-continued

| Phase | Ingredient | INCI | w/w % |
|---|---|---|---|
| | Tea tree oil | *Melaleuca alternifolia* leaf oil | 0.05 |
| | Beta-caryophyllene (90%) | Beta-caryophyllene | 0.1 |
| | Peppermint Essential Oil | *Mentha piperita* oil | 0.05 |
| | Cannabidiol | Cannabidiol | 0.5 |
| | Hemp seed oil | *Cannabis sativa* seed oil | 0.1 |
| pH adjustment | Sodium hydroxide 10% w/v | Sodium hydroxide | 3.0 |
| | Total | | 100.0% |

Example 2

Method of manufacturing: The following procedure was used to produce a laboratory batch according to the formula in Table 1.

I. Preparation of Phase A (Pre-Emulsion)
 Weigh out water into Vessel A.
II. Preparation of Phase B (Aqueous Phase)
 a. Weigh water into Vessel B.
 b. Weigh out glycerin directly in Vessel B under continuous mixing.
 c. Weigh out Carbopol 980 and Xanthan Gum in a weighing boat (e.g. mix physically the powders with a spatula) and add slowly the powder through a stainless-steel mesh (e.g. colander) into Vessel B under continuous mixing at 800 rpm to avoid chunks/aggregates/clumping.
 d. Keep mixing at room temperature for at least 30 minutes to let the polymer swell. Use a flexible spatula to push the polymer from the sides to ensure homogeneity.
III. Preparation of Phase C (Oil Phase)
 a. Individually weigh out the into Vessel C.

| Ingredient | Weighing Vessel |
|---|---|
| Phenoxyethanol | Vessel C direct |
| Isopropyl Myristate | Vessel C direct |
| Tween 80 | Vessel C direct |
| Diethylene glycol monoethyl ether | Vessel C direct |
| Rosemary oil | Vessel C direct |
| Tea tree oil | Vessel C direct |
| Beta-caryophyllene (90%) | Vessel C direct |
| Peppermint essential oil | Vessel C direct |
| Cannabidiol | Weighing boat and then in Vessel C |
| Hemp seed oil | Vessel C direct |

Cover and mix well using lab-scale Heating/Stirring Element at room temperature and protected from light until full dissolution.

IV. Homogenization of Oil Phase (Phase C) into Pre-Emulsion Phase (Phase A)
 Using the homogenizer head, add the Oil Phase (Vessel C)—slowly into Vessel A under continuous homogenization (3000 rpm) and keep homogenizing for 5 min. Mix up and down and side to side to ensure homogeneous emulsion.
V. Homogenization of (Oil Phase B into Emulsion A+C):

a. After 30 minutes of swelling (step 4.2.4), increase the speed of the IKA mixer to 1200-1500 rpm and add Phase A slowly into the Vessel B.
b. Using the spatula, push the gel down onto the stirring element to ensure homogeneity.
c. After 3-4 minutes, add 10% sodium hydroxide dropwise. The viscosity of the mixture should visibly increase significantly, indicating that gelation is happening.
d. Under continual mixing, ensure homogeneity by moving the beaker side to side, up and down and pushing the gel from the sides with a flexible spatula.
e. After 2-3 minutes, reduce the mixing speed gradually and stop mixing.
f. Measure pH of the gel.
g. Discharge bulk product to the designated bulk product container.
h. Place sample at room temperature for stability testing.
i. Repeat pH, viscosity and apply phase separation test 24 hours later.

Example 3

Stability assessment—The composition described in Example 1 was tested for stability for up to 3 months. The physical appearance was monitored for compliance with the specification of "smooth off-white gel". Both pH and viscosity were monitored during the stability study. pH was measured using a standardized pH meter in distilled water. The viscosity was determined with Brookfield Viscometer using a flat spindle CPA52Z at a speed of 0.1-4 RPM at room temperature. After one month of weekly cycling between freezer and ambient room temperature conditions, the composition remained stable. When stored at room temperature for 3 months, the composition also remained stable. The test results are summarized in Table 2:

TABLE 2

Summary of stability test results.

| | Specification | Initial | 1 month | 2 months | 3 months |
|---|---|---|---|---|---|
| Description | smooth off-white gel | complies | complies | complies | complies |
| pH | 5 to 7 | 6.8 | 6.3 | 6.0 | 5.5 |
| Viscosity (centipoise) | 5,000 to 100,000 | 7,000 to 100,000 | 6,000 to 100,000 | 5,000 to 100,000 | 5,000 to 100,000 |

The composition was further tested for phase separation by dispensing about 5 g of product samples into individually labelled centrifuge tubes. Samples were then heated in an oven at 50° C. for 1 hour. After 1 hour, the samples in groups of 8's were centrifuged and run for 30 min at 3500 rpm (i.e. 1900 RCF) for 30 min. The composition remains stable against phase separation and product degradation over a temperature range of at least from about 20 to 50° C. It will be understood by one of ordinary skill in the art that stability of a composition to phase separation will be influenced by the conditions under which the composition was formed and stored.

Example 4

Topical cannabinoid composition for skin hydration and acne-prone skin (Dahlia): An open label, non-randomized, non-controlled trial (ClinicalTrials.gov Identifier: NCT04045119).

This example describes a clinical study to evaluate the short (i.e., after single application) and long-term (i.e., after periodic application) hydrating effects of composition described in Example 1 on facial skin as well as effects on erythema, appearance, instrumentally measured sebum production and quality of life in subjects with oily skin.

Methods

Healthy adult men and women aged 18 to 70 years (n=54) with oily skin were enrolled into a single group, non-randomized, non-controlled, open label trial of composition containing 0.5% cannabidiol. Objectives of the study were to evaluate the short (i.e., after single application) and long-term (i.e., after periodic application) hydrating effects on facial skin as well as effects on erythema, appearance, instrumentally measured sebum production and quality of life. The composition was administered topically to subjects and were evaluated for short term outcomes during their first visit. To evaluate the long-term effects, two other visits were made at intervals of 2 weeks.

Outcomes

Effects on hydration of a single application of the topical preparation on facial skin, through the direct measurement of its electrical properties as an indicator of water content at 1 and 3 hours were the short term and at 2 and 4 weeks were the long-term primary outcome measures. Short term (at 1 and 3 hours) and long term (at 2 and 4 weeks) secondary outcomes were evaluation of change in instrumentally assessed measurement of oily skin; change in instrumentally measured skin biochromophores; subjective assessment of oily skin; skin appearance through standardized photography and investigator evaluation. Other long-term secondary outcomes include assessment of tolerance and acceptance of the test product and quality of life at 2 and 4 weeks.

Inclusion Criteria

Adults over 18 years old men or women with oily or acne-prone skin were included.

Exclusion Criteria

The following is full list of the exclusion criteria:
Pregnant or breast-feeding women.
Subjects with a chronic disease that requires medication.
Subjects with known diagnosis of cancer.
Smoking habit or alcohol consumption habit (i.e., once a day or more).
Recreational or medicinal use of cannabinoids.
Skin diseases (i.e., diseases that require care of a dermatologist).
Current medication uses such as: Immunomodulators, antibiotics, corticoids or retinoids.
Hypersensitivity to any component of the research product.
Involvement in other clinical or cosmetic studies in the last 6 months.
Recent exposure to sun causing sun tanning (i.e., as reported by the subject causing discomfort or change in the usual appearance of the skin).
Permanent decoration of the skin in the test area.

Results

All subjects (n=54) received the treatment and completed the study. The study achieved its primary end point and showed improvement in skin hydration as measured by capacitance at 2 weeks (i.e., after repeated use). Positive effects on subjective appreciations of appearance, clearance and quality of life of subjects with oily or acne-prone skin after the use of the investigational product were reported. Perception of emollient effect was assessed with a score of 7 or higher by most participants suggesting a positive perception of emollient effect, this perception was maintained until the end of the follow up. Most adverse events were mild and resolved spontaneously. After completing long-term follow-up most subjects reported improvement in the appearance of skin A post-hoc analysis showed a significant reduction in the sub-group of subjects with high baseline values (i.e., >150 mg cm2) of sebumetry, this is consistent with a large effect on sebum production in the population.

While the foregoing has presented specific embodiments of the present disclosure, it is to be understood that these embodiments have been presented by way of example only. It is expected that others skilled in the art will perceive variations which, while varying from the foregoing, do not depart from the spirit and scope of the disclosure herein.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this disclosure belongs.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to encompass the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items.

As used herein, whether in the specification or the appended claims, the transitional terms "comprising", "including", "having", "containing", "involving", and the like are to be understood as being inclusive or open-ended (i.e., to mean including but not limited to), and they do not exclude unrecited elements, materials or method steps. Only the transitional phrases "consisting of" and "consisting essentially of", respectively, are closed or semi-closed transitional phrases with respect to claims and exemplary embodiment paragraphs herein. The transitional phrase "consisting of" excludes any element, step, or ingredient which is not specifically recited. The transitional phrase "consisting essentially of" limits the scope to the specified elements, materials or steps and to those that do not materially affect the basic characteristic(s) of the disclosure herein.

The invention claimed is:

1. A topical cannabinoid homogenous gel emulsion composition comprising
   a cannabinoid at 0.1-10% (w/w),
   an antioxidant at 0.01-5% (w/w),
   an anti-microbial agent at 0.01-2% (w/w),
   an anti-inflammatory agent at 0.01-5% (w/w) and
   a skin conditioning agent at 0.01-5% (w/w),
   wherein the topical cannabinoid homogenous gel emulsion composition comprises less than 20% (w/w) of simple polyol,
   wherein the cannabinoid is cannabidiol (CBD),
   wherein the anti-inflammatory agent is beta-caryophyllene, and
   wherein the topical cannabinoid homogenous gel emulsion composition further comprises a humectant at 1-10% (w/w),
   a thickening agent at 0.01-10% (w/w),
   a gel-forming agent at 0.1-5% (w/w),
   a preservative at 0.1-3% (w/w),
   an emollient at 1-3% (w/w),
   a non-ionic surfactant at 1-15% (w/w),
   a penetration enhancer at 1-5% (w/w),
   a fragrance agent at 0.01-2% (w/w),
   a pH adjusting agent in a quantity sufficient for the topical cannabinoid homogenous gel emulsion composition to maintain pH 5-7, and
   water to make up 100% by weight,
   wherein the gel-forming agent is carbomer,
   wherein the emollient is isopropyl myristate, and
   wherein the penetration enhancer is diethylene glycol monoethyl ether.

2. The topical cannabinoid composition of claim 1, wherein the topical cannabinoid homogenous gel emulsion composition comprises no more than 2% (w/w) of simple polyol.

3. The topical cannabinoid homogenous gel emulsion composition of claim 1, wherein the antioxidant and anti-microbial agent are essential anise oil, angelica oil, basil oil, bay oil, bergamot oil, rose oil, camphor oil, cardamom oil, caraway oil, cedar oil, cedarwood oil, chamomile oil, cinnamon oil, citronella oil, clove oil, copaiba balsam oil, cumin oil, coriander oil, dill oil, eucalyptus oil, fennel oil, garlic oil, geranium oil, grapefruit oil, ginger oil, guaiac oil, iris oil, Japanese mint oil, jasmine oil, lavender oil, lemon oil, lemongrass oil, lindera oil, mandarin oil, mint oil, neroli oil, onion oil, orange oil, oregano oil, patchouli oil, parsley oil, pepper oil, peppermint oil, perilla oil, Peru balsam oil, petitgrain oil, pine oil, pine needle oil, rose oil, rosemary oil, sandalwood oil, spearmint oil, star anis oil, sweet orange oil, tangerine oil, tea seed oil, tea tree oil, thyme oil, tolu balsam oil, tuberose oil, turmeric oil, western mint oil, wintergreen oil, combinations, and mixtures thereof.

4. The topical cannabinoid homogenous gel emulsion composition of claim 3, wherein the antioxidant is rosemary oil.

5. The topical cannabinoid homogenous gel emulsion composition of claim 3, wherein the anti-microbial agent is tea tree oil.

6. The topical cannabinoid homogenous gel emulsion composition of claim 1, wherein the skin conditioning agent is avocado oil, canola oil, coconut oil, corn oil, cotton seed oil, flax seed oil, grape seed oil, hemp seed oil, olive oil, palm oil, peanut oil, safflower oil, soybean oil, combinations, and mixtures thereof.

7. The topical cannabinoid homogenous gel emulsion composition of claim 6, wherein the skin conditioning agent is hemp seed oil.

8. The topical cannabinoid homogenous gel emulsion composition of claim 1, wherein the humectant is glycerin, the thickening agent is xanthan gum, the preservative is phenoxyethanol, the non-ionic surfactant is polysorbate 80, the fragrance agent is peppermint essential oil, and the pH adjusting agent is sodium hydroxide.

9. The homogenous gel emulsion of claim 1, wherein the composition has a viscosity in a range of about 5,000 to about 100,000 cps.

10. A method comprising applying the topical cannabinoid homogenous gel emulsion composition of claim 1 to the skin of a subject, wherein the skin of the subject is affected by acne vulgaris.

* * * * *